United States Patent [19]

Menon

[11] 3,954,820
[45] May 4, 1976

[54] PREPARATION OF HYDROCARBYL METAL HALIDES

[75] Inventor: Mannat C. Menon, University Heights, Ohio

[73] Assignee: Ferro Corporation, Cleveland, Ohio

[22] Filed: Feb. 19, 1974

[21] Appl. No.: 443,704

[52] U.S. Cl. .................. 260/429.7; 260/429 R; 260/429.9; 260/437 R; 260/446
[51] Int. Cl.[2] ........................................ C07F 7/22
[58] Field of Search ............ 260/429.7, 437, 429 R, 260/446

[56] References Cited
UNITED STATES PATENTS

| | | | |
|---|---|---|---|
| 3,387,011 | 6/1968 | Coates et al. | 260/429.7 |
| 3,446,826 | 5/1969 | Coates et al. | 260/429.7 |
| 3,449,451 | 6/1969 | Senatore | 260/429.7 |
| 3,519,665 | 7/1970 | Molt et al. | 260/429.7 |

FOREIGN PATENTS OR APPLICATIONS 1,047,389   11/1966   United Kingdom

OTHER PUBLICATIONS

Shapiro et al., The Organic Compounds of Lead, Interscience Publ., N.Y., p. 40 (1968).

Doak et al., Organometallic Compounds of Arsenic, Antimony and Bismuth, Interscience Publ., N.Y., pp. 389–393 (1970).

Nesmeyanov et al., The Organic Compounds of Zinc and Cadmium, North–Holland Publ. Co., Amsterdam, V3, pp. 27 & 28 (1967).

*Primary Examiner*—Helen M. S. Sneed
*Attorney, Agent, or Firm*—Milton L. Simmons; Wesley B. Taylor

[57] ABSTRACT

A process is disclosed for the preparation of hydrocarbyl metal halides, such as alkyl tin chlorides, in which a reaction between the metal in its metallic state and a hydrocarbyl halide is catalyzed by a complex formed between a hydrocarbyl metal halide and a dihydrocarbyl sulfoxide. In the case of tin, for example, the complex may be represented by the formula:

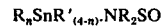

$R_nSnR'_{(4-n)} \cdot NR_2SO$ in which R represents hydrocarbyl substituents, R' represents the halogens, n is a whole number from 1 to 3, inclusive, and N is a whole number from 1 to 5 inclusive.

13 Claims, No Drawings

PREPARATION OF HYDROCARBYL METAL HALIDES

BACKGROUND OF THE INVENTION

Although a number of different metals may be used in the practice of the present process, as hereinafter disclosed, the description of the background and general application of the invention is made with respect to the preferred metal, tin.

Hydrocarbyl substituted tin halides, such as methyl tin chloride, have been found particularly useful in the preparation of derivatives serving as stabilizers for halogenated organic materials, such as polyvinyl chloride resins, chlorinated paraffins, and the like. High purity trialkyl tin compounds including the chlorides are also effective as biocidal compositions.

Various methods have been suggested to prepare hydrocarbyl tin chlorides. To data none has been completely satisfactory. For example, methyl tin chlorides have been prepared commercially by the reaction of Grignard reagent with tin tetrachloride, a process which is expensive and inconvenient to carry out. The Grignard reaction, for instance, produces undesirable side effects. In another process, methyl chloride is bubbled as a vapor through a pool of molten tin or tin alloy held in a vertical reaction tube while heating the tube to a temperature sufficiently high to effect the reaction. This process obviously requires relatively high temperatures, at least higher than that needed to maintain the tin or its alloy in a molten state. At reaction temperatures above about 400°C, alkyl halides begin to decompose thermally. U.S. Pat. No. 2,679,506 also teaches a process for preparing dimethyl tin dichloride in which molten tin is used and at comparatively high temperatures.

Many compounds have been tested as catalysts in a reaction for preparing hydrocarbyl tin halides but have not been found to give entirely satisfactory results. For instance, such compounds are not sufficiently general in their reaction, or provide an insufficient yield of the desired product, or contaminate the hydrocarbyl tin halide with undesirable catalyst residues. Still other processes use expensive catalysts, such as the quarternary onium iodides, and form substantial amounts of by-products. Further, in some prior processes, the conversion rate of tin is rather low, and it is difficult to obtain the desired hydrocarbyl tin halide in a sufficient pure state.

SUMMARY OF THE INVENTION

A principal object of the invention is to provide a process that yields hydrocarbyl metal halides and especially alkyl tin chlorides more easily and less expensively than prior, conventional processes.

The present process prepares hydrocarbyl metal halides from the metal in its free metallic state and in substantially a single step process. The process provides excellent yields, and the product can be used directly for the preparation of heat stabilizers for plastics. The process is less expensive in that both the amount and cost of the catalyst are relatively low in comparison to prior catalysts, and the metal can be used in a less expensive form, for example, shot as compared to powder. In some prior processes, a finely divided form of the metal was used, such as particle sizes of 1 to 300 microns.

In one form, the metallic metal is reacted at a temperature, for example, within the range of about 110°C to about 225°C, in a liquid organic medium in the presence of a catalytic amount of a complex formed between the hydrocarbyl substituted metal halide and a dihydrocarbyl substituted sulfoxide. The hydrocarbyl substituents in the halide and in the sulfoxide may be the same or different, and in all cases are selected from the group consisting of alkyl, isoalkyl, or cycloalkyl, each up to 12 carbon atoms; alkylene, isoalkylene, and cycloalkylene, each up to 12 carbon atoms; alkoxy up to 10 carbon atoms; aryl, alkaryl, aralkyl, halo-substituted aryl, and alkoxy-substituted aryl, each up to 12 carbon atoms.

The preferred metal is tin, although lead, antimony, zinc, cadmium, and admixtures of all of these metals may also be used. The liquid organic medium, used as a heat-transfer agent in the process, may comprise any organic liquid such as benzene, toluene, and the like. However, preferably the liquid organic medium is the hydrocarbyl halide, or the hydrocarbyl substituted metal halide, or a mixture thereof if either is liquid at reaction temperatures and pressures. A preferred product is dialkyl tin dichloride and especially dimethyl tin dichloride.

In one aspect of the present process, the complex which catalyzes the reaction may have this formula:

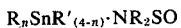

in which R represents a monovalent hydrocarbyl substituent as defined, R' represents the halogens, n is a whole number from 1 to 3 inclusive and N is a whole number from 1 to 5, inclusive.

In the preferred practice, the complex has this formula:

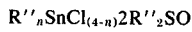

in which R'' represents alkyl, isoalkyl, cycloalkyl, each up to 12 carbon atoms, and n is a whole number from 1 to 3, and N is 2 except that when n is 3, N is 1.

DESCRIPTION OF THE PREFERRED EMBODIMENTS

In one form, the present process comprises preparing a hydrocarbyl substituted metal halide from the metal in its metallic state and a hydrocarbyl halide by reacting the metal and hydrocarbyl halide at a reaction temperature in a liquid organic medium and in the presence of a catalytic amount of a complex formed between the hydrocarbyl substituted metal halide and a dihydrocarbyl substituted sulfoxide.

Considering initially the reactants employed, the metal is preferably tin but may also include lead, antimony, zinc, cadmium, and mixtures of two or more of these five metals. The form of the metal is not critical but preferably is present in a comminuted form. A finely divided particulate form tends to speed the reaction, but one of the advantages of the present process is that the metal may be used in relatively large particle or granular size such as tin or lead shot, mossy zinc, tin foil, metal turnings, and the like.

The hydrocarbyl halide may be represented by the formula RX, in which R is the hydrocarbyl group and X is halogen such as fluorine, iodine, bromine, and preferably chlorine. The dihydrocarbyl substituted sulfoxide used to form the complex may be represented by the formula $R_2SO$ in which R is also the hydrocarbyl group. As used here and in the claims the term "hydrocarbyl" means alkyl, isoalkyl, cycloalkyl, each up to 12 carbon atoms, such as methyl, ethyl, propyl, butyl armyl, octyl, isopropyl, isobutyl, isopentyl, cyclopropyl, cyclohexyl, methylcyclohexyl, and the like; alkylene, isoalkylene, and cycloalkylene each up to 12 carbon atoms such as ethylene, propylene, butylene, isopropylene, isobutylene, isohexylene, cyclopropylene, cyclobutylene, cyclohexylene, etc.; alkoxy up to 10 carbon atoms, such as methoxy, ethoxy, propoxy, etc.; and aryl, alkaryl, aralkyl, halo-substituted aralyl, and alkoxy-substituted aryl, such as phenyl, tolyl, xylyl, ethylphenyl, benzyl, phenylethyl, chlorophenyl, dibromophenyl, bromotolyl, methoxyphenyl, ethoxyphenyl, etc.

The complex which catalyzes the reaction and which is formed by the hydrocarbyl substituted metal halide and the dihydrocarbyl substituted sulfoxide may have this formula:

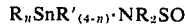

in which R represents a monovalent hydrocarbyl substituent as defined, R' represents all four halogens, n is a whole number from 1 to 3 inclusive, and N is a whole number from 1 to 5 inclusive and preferably 2.

Preferably, the complex has this formula:

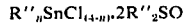

in which R" represents alkyl, isoalkyl, cycloalkyl, each up to 12 carbon atoms, n is a whole number from 1 to 3 inclusive, and N is 2 except that when n is 3, N is 1. When R" is methyl and n is 2, the complex is a white solid having a melting point of 111°C to 113°C. The ratio in the complex of two moles of dimethyl sulfoxide to one mole of dimethyl tin dichloride was confirmed by analysis and infra red spectra.

The process may be carried out by reacting the metal and hydrocarbyl halide at a reaction temperature in a liquid organic medium in the presence of a catalytic amount of the complex. The reaction can proceed at room temperatures (18°C to 30°C) but at a relatively slow rate. It is preferred to employ elevated temperatures such as a temperature within the range of about 110°C to about 225°C and preferably at about 185°C to 200°C. In like manner, pressure is not critical. Atmospheric pressure can be used, although the reaction rate increases with superatmospheric pressures. For instance, pressures up to about 400 psig are useful. Advantageously, the reaction takes place within a closed vessel and autogenous pressure is used, for example, up to about 50 psig. The reaction may be completed with sufficiently high yields in from about two hours to about 50 hours depending on conditions and reactants.

The liquid organic medium merely provides an arena for the reaction to take place by serving as a solvent for the hydrocarbyl halide and the complex. Essentially, the liquid is a heat-transfer medium and, in this form of the invention, should be sufficiently inactive chemically with respect to the reactants and heat-resistant at the temperature of the reaction. A large number of organic liquids and solvents meets these requirements, such as mineral oil, heptane, octane, iso-octane, the cellosolves, isooctyl, thioglycloate, kerosene, fuel oil, the glycols such as ethylene glycol, tetrahydrofuran, dibutyl ether and the like.

As indicated, the complex catalyzes a reaction between the metal in its metallic state and the hydrocarbyl halide to form the hydrocarbyl metal halide. The complex can be added as such to the reaction medium, but preferably it is formed in situ. In this practice of the invention, an initial reaction between the metal and hydrocarbyl halide takes place to form a hydrocarbyl metal halide. Some of this halide reacts with the dihydrocarbyl sulfoxide also present in the reaction medium to form the complex. The complex then catalyzes further reaction between the metal and hydrocarbyl halide. For example, in the case of tin and methyl chloride and dimethyl sulfoxide, the reactions may be represented as follows:

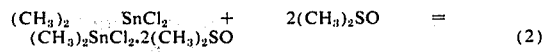

The hydrocarbyl halide should be present in stoichiometric excess with respect to the metal over the indicated 2:1 molar ratio, for example about 50% weight excess, not only to make that reaction proceed, but also because some of the resulting dihydrocarbyl metal halide reacts with the dihydrocarbyl sulfoxide to form the complex. The amount of the dihydrocarbyl sulfoxide used can be regulated to provide a catalytic amount of the complex, for example, an amount of about 1.5% to about 10% and preferably about 3.5% based on the weight of the dihydrocarbyl sulfoxide to the weight of the metal. In this manner, the over-all net effect is that the complex catalyzes a reaction between the metal and the hydrocarbyl halide to form the hydrocarbyl substituted metal halide. The preferred product is dimethyl tin dichloride.

In an improved form of the invention, the function of the liquid organic medium is supplied by one of the reactants itself, if such reactant is liquid under the conditions of the reaction. For example, if either the hydrocarbyl halide or the hydrocarbyl substituted metal halide is liquid under the temperature and pressure conditions of the reaction, it can supplant the use of a non-reactive, inert organic liquid previously described. As examples, propyl chloride, butyl chloride, dimethyl tin dichloride, and dibutyl tin dichloride are liquid at either room temperatures or at the usual elevated temperatures and pressures at which the catalyzed process usually takes place. They can therefore be used, especially under pressure, as the heat-transfer medium as well as a reactant of the reaction. On the other hand, methyl chloride is normally a gas and cannot be used in this manner.

The following examples are intended only to illustrate the invention and should not be construed to impose limitations on the claims. Compositions are by weight precent unless otherwise indicated.

EXAMPLE 1

This example illustrates the use of an organic liquid, which is not a reactant, as the reaction medium. The following reactants were added to a Parr bomb:

| Reactant | Grams |
|---|---|
| Isooctyl thioglycolate (heat transfer medium) | 194 |
| Tin shot | 416 |
| Dimethyl tin dichloride | 88 |

-continued

| Reactant | Grams |
| --- | --- |
| Dimethyl sulfoxide | 15.6 |

Methyl chloride gas was pumped into the bomb as it was heated within the range of 140°C to 190°C for 25 hours until 302 grams of methyl chloride had been added. A maximum pressure of 50 psig was reached in the bomb. Some of the dimethyl tin dichloride reacted with all of the dimethyl sulfoxide to form the catalytic complex. Thus, there was a 3.75% catalyst present based on the weight of the dimethyl sulfoxide to the weight of the tin, or 9.1% by weight of the catalytic complex based on the weight of the tin.

The reaction produced a yield of 85.5% of dimethyl tin dichloride based on the methyl chloride consumption.

EXAMPLE 2

This example also illustrated the use of an inert, non-reactive organic liquid as the liquid support or heat transfer medium. A procedure was carried out like the procedure of Example 1 in which the following reactants were added to the Parr bomb:

| Reactant | Grams |
| --- | --- |
| Mineral Oil (about 300 milliliters, liquid support) | 250 |
| Tin Shot | 118.7 |
| Dimethyl sulfoxide | 4.5 |
| Dimethyl tin dichloride | 23.7 |

Methyl chloride gas was bubbled into the reaction medium with the Parr bomb closed until 45 grams had been added. Meanwhile the bomb was maintained at a temperature within the range of 180°C to 192°C for 15.5 hours. The catalytic complex was formed in situ and amounted to 3.75% based on the weight of the dimethyl sulfoxide to the weight of the tin, or 9.1% by weight of the catalytic complex based on the weight of the tin. There was a yield of 40.2% of dimethyl tin dichloride based on the weight of the tin.

EXAMPLE 3

In the following example, one of the reactants formed the liquid support or heat transfer medium for the reactants:

| Reactant | Grams |
| --- | --- |
| Dimethyl tin dichloride (liquid support) | 400 |
| Tin shot | 416 |
| Dimethyl sulfoxide | 14.7 |

Methyl chloride gas was bubbled into the reaction medium with the Parr bomb closed until 361 grams had been added. Meanwhile, the bomb was maintained at a temperature within the range of 140°C to 195°C for 13 hours. The catalytic complex was formed in situ and amounted to 8.5% by weight based on the weight of the tin. There was a yield of dimethyl tin dichloride of 100% based on the weight of the tin, that is, all tin was consumed.

EXAMPLE 4

In this example, the following reactants were charged to a Parr bomb:

| Reactant | Grams |
| --- | --- |
| Dimethyl tin dichloride (liquid support) | 400 |
| Tin shot | 416 |
| Dimethyl sulfoxide | 15.6 |

Methyl chloride gas was pumped into the closed bomb until 340 grams had been added. The bomb was maintained at a temperature within the range of 152°C to 192°C for 11 to 12 hours. The catalytic complex was formed in situ and amounted to comprised 3.75% based on the weight of the sulfoxide to the weight of the tin. There was a yield of dimethyl tin dichloride of 96.3% based on methyl chloride consumption.

EXAMPLE 5

In this example, the catalytic complex was prepared prior to its addition to a Parr bomb and amounted to 9% by weight based on the weight of the tin. These ingredients were added to the bomb.

| Reactant | Grams |
| --- | --- |
| Crude dimethyl tin dichloride formed from Example 4 (liquid support) | 420 |
| Tin shot | 416 |

An amount of 15.6 grams of dimethyl sulfoxide and 43.4 grams of dimethyl tin dichloride were mixed together and the mixture added to the bomb. Methyl chloride gas was then pumped into the closed bomb until 356 grams had been added. The bomb was maintained at a temperature within the range of 165°C to 190°C for 11 to 12 hours. There was a yield of 100% of dimethyl tin dichloride based on methyl chloride consumption.

EXAMPLE 6

In this example the catalytic complex was also prepared prior to its addition to the bomb. The complex amounted to 5.8% based on the weight of tin used. These reactants were added to the Parr bomb:

| Reactant | Grams |
| --- | --- |
| Crude dimethyl tin dichloride obtained from Example 4 (liquid support) | 435 |
| Tin shot | 416 |

Ten grams of dimethyl sulfoxide and 40 grams of dimethyl tin dichloride were mixed together and the mixture added to the bomb. Methyl chloride gas was added to the reaction bomb until 359 grams had been added. The bomb was maintained at a temperature within the range of 157°C to 191°C for 11 to 12 hours. There was a yield of 100% of dimethyl tin dichloride based on methyl chloride consumption.

EXAMPLE 7

The catalytic complex, amounting to 24.4% based on the weight of the tin was prepared prior to its addition to the bomb in this example. The reactants in the Parr bomb included:

| Reactant | Grams |
| --- | --- |
| Dimethyl tin dichloride (liquid support) | 400 |
| Tin shot | 237 |
| Dimethyl sulfoxide | 24 |
| Dimethyl tin dichloride | 40 |

An amount of 186 grams of methyl chloride gas was added to the closed bomb while it was maintained at a temperature of 150°C to 220°C for 7.75 hours. There was a yield of 82% of dimethyl tin dichloride based on methyl chloride consumption.

EXAMPLE 8

The reactants added to the Parr bomb for this example were:

| Reactant | Grams |
| --- | --- |
| Dimethyl tin dichloride (liquid support) | 400 |
| Tin shot | 416 |
| Dimethyl sulfoxide | 15.6 |

While the bomb was maintained at a temperature within the range of about 152°C to 195°C for 43.75 hours, 332 grams of methyl chloride gas was added. There was a yield of 94% of dimethyl tin dichloride based on methyl chloride consumption.

The time for this run was extended in order to determine the effect of temperature and methyl chloride pressure on the rate of the reaction, while using 3.75% dimethyl sulfoxide based on the weight of the tin to form the complex and dimethyl tin dichloride as the heat transfer medium or liquid carrier. The results are given in Table A as grams of methyl chloride absorbed per hour.

TABLE A

| Temp. °C | $CH_3Cl$ Pressure Psig | Reaction Rate Gms. $CH_3Cl$ per Hr. |
| --- | --- | --- |
| 160–165 | 50 | 8.5 |
| 170–175 | 50 | 16.0 |
| 185–190 | 50 | 29.0 |
| 185–190 | 15 | 14.0 |
| 185–190 | 30 | 19.0 |

EXAMPLE 9

This example illustrates the effect of the present complex as a catalyst in the reaction in comparison with another type of dialkyl sulfurcontaining compound. These reactants were added to a Parr bomb:

| Reactant | Grams |
| --- | --- |
| Dimethyl tin dichloride (liquid support) | 400 |
| Tin shot | 237 |
| Dimethyl sulfone (catalyst) | 23.7 |

Methyl chloride gas was added to the bomb in plentiful supply to assure that all methyl chloride gas capable of entering into any reaction was available. Meanwhile, the bomb was maintained at a temperature within the range of 160°C to 192°C for 44.5 hours. There was an extremely low yield of dimethyl tin dichloride amounting to less than 10% based on methyl chloride consumption. The amount was so small that the 10% represents an estimate based on the unreacted tin.

EXAMPLE 10

In this and the following examples, n-butyl chloride or dibutyl tin dichloride was used as the heat transfer medium. Temperatures up to about 170°C and bomb pressures up to about 125 psig were met.

The following reactants were added to a Parr bomb.

| Reactant | Grams |
| --- | --- |
| Dibutyl tin dichloride (liquid support) | 300 |
| Tin shot | 59.4 |
| n-Butyl chloride | 92.5 |
| Dimethyl sulfoxide | 6.0 |

The bomb was heated at a temperature within the range of 150°C to 190°C for 12 hours. The catalytic complex was formed in situ by reaction between the dibutyl tin dichloride and dimethyl sulfoxide. The catalyst amounted to 10% based on the weight of the dimethyl sulfoxide to the weight of the tin. There was a yield of butyl tin chlorides of 66% based on the amount of tin residue, that is, 66% by weight of the tin had been consumed. At least 75% of the product was monobutyl tin dichloride and dibutyl tin dichloride.

EXAMPLE 11

The following reactants were added to a Parr bomb:

| Reactant | Grams |
| --- | --- |
| n-Butyl chloride (liquid support) | 555 |
| Tin shot | 357 |
| Catalytic complex of dimethyl sulfoxide and dimethyl tin dichloride | 43 |

The catalytic complex was added to the bomb rather than forming it in situ and amounted to 12% based on the weight of the tin. The bomb was maintained at a temperature within the range of 86°C to 170°C for 23.5 hours. A yield of butyl tin chlorides was obtained of 38% based on the amount of tin residue.

EXAMPLE 12

The reactants in the Parr bomb of this example were:

| Reactant | Grams |
| --- | --- |
| n-Butyl chloride (liquid support) | 370 |
| Tin shot | 237.4 |
| Dimethyl sulfoxide | 32.7 |
| Dibutyl tin dichloride | 92.0 |

The catalyst was formed in situ from the last two named reactants and amounted to 29.2% of the complex based on the weight of the tin. The bomb was maintained at a temperature in the range of 100°C to 167°C for 18 hours and yielded 35.8% of butyl tin chlorides based on the amount of tin residue.

EXAMPLE 13

This example illustrates the effect of the present catalytic complex in comparison with another material attempted to be used as a catalyst. The reactants in a Parr bomb included:

| Reactant | Grams |
| --- | --- |
| n-Butyl chloride (liquid support) | 278 |
| Tin shot | 118.7 |
| Sodium iodide (catalyst) | 12 |

The catalyst amounted to about 10% based on the weight of the tin. The bomb was maintained at a temperature in the range of 168°C to 170°C for 6 hours. There was a yield of butyl tin chlorides of 1.2% based on the amount of tin residue, that is, 98.8% of the tin was unreacted.

EXAMPLE 14

The following reactants were used:

| Reactant | Grams |
| --- | --- |
| n-Butyl chloride (liquid support) | 278 |
| Tin shot | 118.7 |
| Dimethyl sulfoxide | 23.8 |
| Dibutyl tin dichloride | 51.0 |

The last two mentioned reactants were mixed together prior to admixture with the other reactants in a bomb. The catalyst amounted to about 20% based on the weight of the sulfoxide to the weight of the tin. The bomb containing the reactants was maintained at a temperature in the range of 166°C to 175°C for 20 hours. There was a yield of 100% of butyl tin chlorides based on the absence of any tin residue.

EXAMPLE 15

The reactants placed in a Parr bomb were:

| Reactant | Grams |
| --- | --- |
| n-Butyl chloride (liquid support) | 278 |
| Tin shot | 118.7 |
| Dimethyl sulfoxide | 12.0 |
| Dibutyl tin dichloride | 25.8 |

The catalyst was prepared from the last two reactants prior to admixture with the other reactants and amounted to 10% based on the weight of the sulfoxide to the weight of the tin. The bomb was heated at a temperature within the range of 170°C to 175°C for 20 hours and produced a yield of 70% butyl tin chlorides based on the amount of tin residue. It will be noted that the reduction in yield in this example as compared to Example 14 is accompanied with a reduction in the relative amount of catalyst used.

EXAMPLE 16

In this example the following reactants were added to a Parr bomb:

| Reactant | Grams |
| --- | --- |
| n-Butyl chloride (liquid support) | 278 |
| Tin shot | 118.7 |
| Dibutyl sulfoxide | 23.7 |
| Dibutyl tin dichloride | 24.4 |

The catalyst was prepared from the last two named ingredients prior to addition to the bomb. The bomb was heated at a temperature in the range of 165°C to 172°C for 15.5 hours. There was a yield of butyl tin chlorides of 49.3% based on the amount of tin residue.

EXAMPLE 17

The following reactants were added to a Parr bomb:

| Reactant | Grams |
| --- | --- |
| n-Butyl chloride (liquid support) | 278 |
| Tin shot | 118.7 |
| Dimethyl sulfoxide | 12.0 |
| Dibutyl tin dichloride | 25.8 |

The catalyst was prepared prior to addition to the bomb. The bomb was heated at a temperature in the range of 190°C to 195°C for 20 hours, yielding 91% butyl tin chlorides based on the amount of tin residue.

The present process may also be continuous. In this case the catalytic complex remains active. Only make-up catalytic complex is needed to account for small physical losses. Using greater amounts of catalyst than about 10% (based on weight ratios of the disulfoxide to the metal) does not reduce the reaction time proportionately, and therefore use of greater than 10% of catalyst is largely wasteful. Yield of a crude product, such as the dimethyl tin dichloride in Example 3, was 100% in many instances, and the crude product could be used directly for further processing since it usually was 95% pure or better.

For purposes of comparison, especially as to yield and purity of product, the reactants used in the foregoing examples were somewhat standardized. It is understood, however, that other metals and other hydrocarbyl groups, as previously disclosed, could have been substituted for those indicated.

The sulfoxide moiety is the useful part of the catalytic complex. For this reason the hydrocarbyl portions of the complex can be varied substantially as disclosed. Other sulfur-containing radicals, such as sulfone, or a sulfide catalyze little or no reaction of the type herein contemplated. On the other hand, the complex as defined can be formed by other reactions than one between a hydrocarbyl substituted metal halide and a dihydrocarbyl substituted sulfoxide. Recitation of this reaction as in the claims is intended to be only illustrative of one manner by which the complex is formed. It may, for example, be formed by other reactions such as a reaction between a hydrocarbyl substituted metal halide and a trialkyl sulfoxonium halide such as trimethyl sulfoxonium chloride.

Although the foregoing discloses several embodiments of the present invention, it is understood that the invention may be practiced in still other forms within the scope of the following claims.

I claim:
1. A catalytic process for preparing a hydrocarbyl substituted tin halide from tin in its metallic state and a hydrocarbyl halide, comprising: catalytically reacting the metallic tin and hydrocarbyl halide at a reaction temperature in a liquid organic heat-transfer medium in the presence of a catalytic amount of a catalyst consisting essentially of a complex formed between said hydrocarbyl substituted tin halide and a dihydrocarbyl substituted sulfoxide, said liquid medium being a solvent for the hydrocarbyl halide and complex, said hydrocarbyl substituents in said halide and said sulfoxide being the same or different and in all cases being se- lected from the group consisting of alkyl, isoalkyl, or cycloalkyl, each up to 12 carbon atoms, and alkenyl, isoalkenyl, and cycloalkenyl, each up to 12 carbon atoms.

2. The process of claim 1 in which said hydrocarbyl-substituted metal halide is a dialkyl tin dichloride.

3. The process of claim 1 in which said reaction temperature is within the range of about 110°C to about 225°C.

4. The process of claim 1 in which said liquid organic medium is selected from the group consisting of said hydrocarbyl halide if liquid at room temperatures, said hydrocarbyl substituted metal halide, and a mixture thereof.

5. A catalytic process for preparing a hydrocarbyl-substituted tin halide from metallic tin and a hydrocarbyl halide, comprising: catalytically reacting the metallic tin with the hydrocarbyl halide at a temperature within the range of about 110°C to about 225°C in a liquid medium selected from the group consisting of a hydrocarbyl halide if liquid at room temperatures, a hydrocarbyl-substituted tin halide, and mixtures thereof in the presence of a catalytic amount of a catalyst consisting essentially of a complex formed between said hydrocarbyl substituted tin halide and a dihydrocarbyl substituted sulfoxide, said hydrocarbyl substituents in said halide and said sulfoxide being the same or different and in all cases being selected from the group consisting of alkyl, isoalkyl, and cycloalkyl, each up to 12 carbon atoms, and alkenyl, isoalkenyl, and cycloalkenyl, each up to 12 carbon atoms.

6. The process of claim 5 in which said hydrocarbyl-substituted tin halide is dimethyl tin dichloride.

7. The process of claim 5 in which said hydrocarbyl halide is methyl chloride and said liquid medium is said hydrocarbyl-substituted tin halide.

8. The process of claim 5 in which said reaction is carried out in an enclosed reaction chamber of autogeneous pressure.

9. The process of claim 5 in which said complex has the formula:

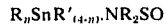

in which R represents a monovalent hydrocarbyl substituent as defined, R' represents the halogens, $n$ is a whole number from 1 to 3 inclusive, and N is a whole number from 1 to 5, inclusive.

10. A catalytic process for preparing an alkyl tin chloride from metallic tin and an alkyl chloride, comprising: catalytically reacting the metallic tin with the hydrocarbyl halide at a temperature within the range of about 110°C to about 225°C in a liquid medium selected from the group consisting of an alkyl chloride liquid at room temperatures, said alkyl tin chloride, and mixtures thereof, said alkyl groups containing up to 12 carbon atoms, in the presence of a catalytic amount of a catalyst consisting essentially of a complex having the formula:

$$R''_n SnCl_{(4-n)} \cdot NR''_2 SO$$

in which R'' represents alkyl, isoalkyl, cycloalkyl, each up to 12 carbon atoms, and $n$ is a whole number from 1 to 3 inclusive, and N is 2 except that when $n$ is 3, N is 1.

11. The process of claim 10 in which said alkyl tin chloride is dimethyl tin dichloride.

12. The process of claim 10 in which said alkyl chloride is methyl chloride and said liquid medium is an alkyl tin chloride.

13. A process of claim 10 in which said reaction is carried out in an enclosed reaction chamber and at autogenous pressure.

* * * * *